US005698208A

United States Patent [19]
Nigg et al.

[11] Patent Number: 5,698,208
[45] Date of Patent: Dec. 16, 1997

[54] USE OF BORAX TOXICANTS TO CONTROL TEPHRITIDAE FRUIT FLIES

[75] Inventors: Herbert N. Nigg; Samuel E. Simpson, both of Lake Alfred, Fla.

[73] Assignee: University of Florida, Gainesville, Fla.

[21] Appl. No.: 530,035

[22] Filed: Sep. 19, 1995

[51] Int. Cl.$^6$ ..................................... A01N 25/02
[52] U.S. Cl. ................ 424/405; 424/408; 424/410; 424/84; 424/658; 424/659
[58] Field of Search ........................ 424/658–660, 424/405–418, 84, 421

[56] References Cited

U.S. PATENT DOCUMENTS

| | | | |
|---|---|---|---|
| 4,840,800 | 6/1989 | Harris | 426/2 |
| 4,873,084 | 10/1989 | Sallay | 424/658 |
| 4,877,607 | 10/1989 | McGovern et al. | 424/84 |
| 5,243,781 | 9/1993 | Carter | 43/112 |
| 5,516,520 | 5/1996 | Yang et al. | 424/408 |

*Primary Examiner*—Neil S. Levy
*Attorney, Agent, or Firm*—Saliwanchik, Lloyd & Saliwanchik

[57] ABSTRACT

Methods and compositions, which rely upon borax toxicants, to control Tephritidae fruit fly populations below economic thresholds are disclosed. More particularly, methods and compositions which utilize borax toxicants are disclosed which cause the Tephritidae fruit flies to die prematurely or which interfere with the female Tephritidae fruit flies to produce eggs for a period of about seven days. A preferred borax toxicant is borax wherein an effective amount in the compositions to accomplish the above is between at least about 0.01M and about 0.12M or more. A lethal amount of borax that should be consumed by the fruit flies in about a 24 hour period is believed to be between at least about 5 mM and about 10 mM or more, whereas the amount of borax that should be consumed by the female fruit flies within about a 24 hour period to prevent the female fruit flies from producing eggs for about seven days or longer is believed to be at least about 2.5 mM and 5 mM or more.

30 Claims, No Drawings

USE OF BORAX TOXICANTS TO CONTROL TEPHRITIDAE FRUIT FLIES

FIELD OF THE INVENTION

The present invention relates to compositions and methods utilizing borax toxicants, such as borax, to control fruit fly populations of the Tephritidae family.

BACKGROUND

Roaches, ants, termites, house flies and fruit flies are common pests that have plagued mankind for ages. House flies are serious nuisance pests to the poultry and livestock industries, whereas fruit flies are a serious problem to, for example, citrus fruit, and have continued to plague agricultural industry for decades. Extensive efforts have been made heretofore to exterminate these difficult and sometimes disease-bearing and/or fruit infecting insects.

Boric acid is known as a killing agent in roach, fruit fly and ant-killing compositions. For example, Australian patent 22,579 (Fenwicke, 1935) teaches the use of boric acid as a "germicidal antiseptic" in combination with castor oil and turpentine as "cleaning agents" to be applied to sheep for killing maggots. Japanese patents J5-8052-205 (Nakamoto, 1981 ), J6-1030-506-A (Watkayama, 1984) and J6-1078-705-A (Amachir, 1984) teach the use of boric acid as the killing agent in various complex compositions for killing roaches (Nakamoto and Amachir) and white ants (Wakayama). All three Japanese patents are dried and used in a pellet, tablet or ball form. Enkerlin, W. et al.: Use of a Mixture of Boric Acid, Borax, Hydrolyzed Protein, and Water to Control Anastrepha Fruit Flies, *Fruit Flies: Biology and Management*, ed. Alua, P. and Liedo, P., Springer-Verlag, N.Y., Inc., pp. 353-358 (1993) discusses the use of a toxic bait consisting of boric acid, hydrolyzed protein (PIB.7) and water to kill, for instance adult *Anastrepha Ludens* (Loew) and adult *Ceratitis capitaia* (Wied).

French patent 2,491,296 (Lagache, 1982) shows a 50/50 by weight composition of boric acid or one of its salts plus sweetened condensed milk which was placed, without spreading, in a ship's hold to control cockroaches. Japanese document JA-72-23198-R (Sankyo Co. Ltd. 47-23198) shows a toxic roach bait comprising insecticidal compositions, e.g. dieldrin, BHC (Lindane), DDT, Sumithic, and boric acid mixed With more than 4 weight percent glycerol in carriers, such as cereal, fish meal, rice bran, starch paste, sugar, realrose, fatty acids, faulty acid esters and fatty alcohols. Japanese patent J5-4017-120 (Sakamoto) shows a cockroach bait of 1.5–10 weight percent boric acid, 10–50 weight percent starch and an extract of fish or animal bones prepared by boiling the bones in water for not over 2 hours.

While boric acid has been used previously, the art teaches that it must be kept dry, as wet boric acid will not work; Wellness Letter, University of Calif. at Berkeley, September 1991, page 7. Thus, use of boric acid with aqueous liquefiers, such as water, is not expected to be effective.

U.S. Pat. No. 4,205,066 (Hennant et al.) discloses a bait composition for anthropophilic flies which utilizes boric acid, for example, as the insecticidal material in such bait compositions.

U.S. Pat. No. 4,440,746 (Maglio) is concerned with a granular pesticide composition which relies upon borax as a source of borate ions to effect gelation of polyvinyl alcohol.

U.S. Pat. No. 4,617,188 (Page) relates to natural insecticides employing borax and carob to control cockroaches.

Grace, J. K. et al.: *J. Econ. Entomol*, 84(6):1753–1757 (1991 ) is concerned with the response of certain subterranean termites to borate dust and soil treatments.

Enkerlin, W. et al.: Use of a Mixture of Boric Acid, Borax, Hydrolyzed Protein, and Water to Control Anastrepha Fruit Flies, *Fruit Flies: Biology and Management*, ed. Aluja, P. and Liedo, P., Springer-Verlag, N.Y., Inc., pp. 353–358 (1993) suggest that borate compounds may be used as insecticides against fruit flies and that a mixture of boric acid, borax, hydrolyzed protein and water may be used to control Anastrepha fruit flies.

Hogsette, J. A. et al.: *J. Econ. Entomol.*, 85(4): 1209–1212 (1992) compare toxicity of aqueous solutions of boric acid and polybor (disodium octaborate tetrahydrate) to house flies (Diptera: Muscidae).

Mullens, B. A. et al.: *J. Econ. Entomol.*, 85(1):137–143 (1992) is concerned with the effects of disodium octaborate tetrahydrate (polybor) on the survival, behavior and egg viability of adult Muscoid flies (Diptera: Muscidae), i.e., house flies.

Lopez, F. D. et al.: *J. Econ. Entomol.*, 61(1):316–317 (1968) disclose the use of pelletized lures formulated with borax and either PIB.7 (protein insect bait) or ENT-44, 014-X (enzyme hydrolyzed cottonseed protein) to trap and catch Mexican fruit flies.

Lopez, F. D. et al.: *J. Econ. Entomol.*, 60(1):137–140 (1967) suggest that sodium borate inhibits decomposition of two protein hydrolysates attractive to the Mexican fruit fly.

Ken, A. J. et al.: *Insect Pests Leaflets, Noll.-Fruit Flies*, Gov't Printer, Dept. of Agriculture, N.S.W. Australia (1930) disclose the use of lures containing borax to trap Mediterranean and Queensland fruit flies.

Newman, L. J. et al.: *Fruit Fly (Ceratitis capitata); Baiting and Trapping Experiments*, leaflet No. 244, Gov't Printer, Dept. of Agriculture, Western Australia disclose the use of arsenate of soda as a rapid killer of certain fruit flies and that trapping or luring methods utilizing arsenate of soda appear to be somewhat more effective than baiting methods.

The prior art also shows the high degree of specificity of attractants in different insecticide compositions. For example, U.S. Pat. No. 4,049,460 (Broadbent, 1977), teaches a composition of brown sugar, a binder material (paraffin or wax), dry dog food, maltose ad Dursban (a commercially available insecticide) in pellet form. Roaches are attracted to the dog food, maltose and sugar mixture. The pellets are coated with paraffin or wax to protect them from disintegrating upon exposure to environmental factors. The Dursban is ingested by the roaches, along with the attractant. Japanese patent J53091-140 (Kao Soap KK) teaches the use of pure concentrated sesame oil, preferably mixed with an extract of cockroaches faeces as an attractant for cockroaches.

U.S. Pat. No. 4,332,792 (Kohn et al., 1982) teaches a process for preparing a pyrolyzate solution of corn syrup and N-methylnicotinic acid for attracting insects, particularly roaches.

U.S. Pat. No. 4,369,176 (Ott, 1983) teaches a sugar, bacteria and carrier material (such as ground corncobs, sawdust or sand) for use as an insect attractant. The sugar is degraded by the bacteria, causing fermentation by-products which are the attractant. The attractant is combined with an insecticide to kill insects. The insects ingest the insecticide along with the composition.

U.S. Pat. No. 4627,981 (Shimano et al., 1986) discloses the use of various alcohols dissolved in an organic solvent and impregnated on a carrier (such as cardboard or cloth) for use in attracting and killing insects in pellet form.

Notwithstanding the above, there is still a need in the art for improved toxicants that are effective against fruit flies of the family Tephritidae and that are specific and powerful attractants, that have features for direct and easy application, and that are not environmental pollutants or potential carcinogens.

SUMMARY OF THE INVENTION

In brief, the present invention overcomes and alleviates certain of the above-mentioned drawbacks and shortcomings of the prior art and is directed to novel methods and compositions for attracting and either killing or controlling reproduction of fruit flies of the family Tephritidae.

Generally speaking, the present invention is premised upon the realization that borax or borate compounds in effective amounts will not only attract fruit flies, but will either kill fruit flies or cause female fruit flies to stop producing eggs for at least about seven days, depending upon the amount formulated into the bait or lure and ingested by the fruit flies. While the preferred toxicant contemplated by the present invention is borax (sodium borate decahydrate-10 mol $Na_2B_4O_7 \cdot 10H_2O$ or sodium borate pentahydrate-5 mol $Na_2B_4O_7 \cdot 5H_2O$), other suitable borate compounds may be utilized in effective amounts as substitutes for borax or may be utilized in effective amounts in combination with borax or one another. Exemplary of borax-type compounds envisioned by the present invention include anhydrous borax $Na_2B_4O_7$, ammonium tetraborate $(NH_4)_2B_4O_7 \cdot 4H_2O$, ammonium pentaborate $(NH_4)_2B_{10}O_{16} \cdot 8H_2O$, potassium pentaborate $K_2B_{10}O_{16} \cdot 8H_2O$, potassium tetraborate $K_2B_4O_7 \cdot 4H_2O$, sodium metaborate (8 mol) $Na_2B_2O_4 \cdot 8H_2O$, sodium metaborate (4 mol) $Na_2B_2O_4 \cdot 4H_2O$, disodium tetraborate decahydrate $Na_2B_4O_7 \cdot 10H_2O$, disodium tetraborate pentahydrate $Na_2B_4O_7 \cdot 5H_2O$ and disodium octaborate tetrahydrate $Na_2B_8O_{13} \cdot 4H_2O$. Thus, the term "borax toxicant(s)" is used herein broadly and includes collectively and/or individually such borax and any other suitable borax type compounds.

Also in accordance with the present invention, the borax toxicants may be utilized alone or in combination with baits, insecticides, other toxicants, agars, liquefiers, sweeteners, carriers and the like. Moreover, the borax toxicants may be utilized in the anhydrous and hydrous forms; however, when the anhydrous forms are selected, it should be appreciated by those versed in this art that such compounds are typically more expensive and will generally convert to a hydrated form in water or moisture environments. It should also be appreciated by those versed in this art that mixtures of borax toxicants may be utilized, as long as the borax toxicant available in such mixtures achieves the proper molarity to ensure that the objectives of the present invention are not defeated.

In accordance with the present invention, an effective molarity for a borax toxicant is believed to be in the range of between about 0.02M and about 0.12M or higher. When the end result to be accomplished is to kill fruit flies of the Tephritidae family, the amount of a borax toxicant that is believed that should be ingested by a fruit fly is between about 5 micromoles and about 10 micromoles during about a 24 hour period of time. However, if the objective is to prevent or stop the female fruit flies from laying eggs for about seven days or more, the borax toxicant concentrate may be adjusted, so that the amount ingested by a female fruit fly is believe to be between about 2.5 micromoles and about 5.0 micromoles during about a 24 hour period of time. It should be appreciated by those of skill in this art that the fruit flies of the Tephritidae family, as contemplated by the present invention, include the Caribbean fruit flies, the Mediterranean fruit flies, the Mexican fruit flies, the Oriental fruit flies and any other fruit flies which may be controlled by the methods and compositions of the present invention.

In accordance with the present invention, the methods and compositions are believed to be safe and effective and, therefore, can be used on any surface or at any location, such as paper, cardboard, concrete, plastic, metal, glass, plants, in kitchens of homes and restaurants, trees, utility poles, fences, signs, etc. In addition, the compositions of the present invention can be easily applied directly to areas of infestation and will remain active for extended periods of time. Therefore, the borax toxicants of the present invention may be used in residential preparations, commercial crop production, eradication programs and suppression programs for Tephritid fruit fly control.

In accordance with the present invention, the compositions include a mixture of a borax toxicant in an effective amount and, for example, protein hydrolysate bait or any synthetic bait to generate a bait or lure in the form of a patty, heavy cream, pellet, gel, foam, paste, liquid or spray. An example of a patty in accordance with the present invention includes borax in an amount of between about 0.01M and about 0.1M or more, agar, yeast hydrolysate, sugar and water. Notwithstanding, the bait or lure may be in the free form or, alternatively, in a form, such as granules or tablets, agglomerated with or without the aid of a binder, Moreover, the bait or lure can be fixed or impregnated on a support or absorbed therein, and this support may include, for instance, agar, paper, cardboard, plastic such as polystyrene, polyvinyl chloride, polyvinyl acetate and cellulose acetate, glass, pumice, crushed marble, silica or silica minerals. Optionally, other toxicants, such as Malathion, Dibrom® and Naled®, attractants, such as Male Lure 11® and methyl eugenol, sweeteners, carriers and/or liquefiers may be used as indicated hereinbefore. The bait or lure may then be placed in selected locations such that the fruit flies are likely to encounter and ingest the borax toxicant to assure the desired effect, but preferably out of the way of normal human or animal traffic.

It should therefore now be understood by those versed in this art that the novel methods and compositions of the present invention provide a simple, yet unique solution to controlling fruit fly populations by providing an attractant and a food arrestant for fruit flies. More particularly, it has been surprisingly discovered that the methods and compositions of the present invention uniquely attract the fruit flies and cause the fruit flies to stay and engorge, so that the objectives of the present invention are accomplished, i.e., controlling the population of fruit flies by either killing the fruit flies or preventing the female fruit flies from producing eggs for at least about a seven day period.

The above features and advantages of the present invention will be better understood with reference to the detailed description and examples set out hereinafter. It will also be understood that the methods and compositions of this invention are exemplary only and are not to be regarded as limitations of this invention.

DETAILED DESCRIPTION

By way of illustrating and providing a more complete appreciation of the present invention and many of the attendant advantages thereof, the following detailed description is provided covering the novel methods and compositions which utilize borax toxicants to eradicate or control fruit flies. Moreover, the following detailed description illustrates the invention by way of example, not by way of limitation of the principles of the invention. This detailed description should therefore enable one skilled in the art to make and use the inventions and describes several embodiments, adaptations, variations, alternatives and uses of the invention, including what is presently believed to be the best mode of carrying out the invention.

One objective of the present invention is in wide-area suppression and eradication programs. Currently, hard pesticides, such as malathion, are formulated with a protein hydrolysate bait, such as Miller's Nu-Lure®. The protein hydrolysates are usually corn-based. Instead of the hard pesticide, one of the borates detailed above, and especially borax, may be substituted in one of the concentrations previously described. This substitution results in a pH change from about 5.0 to 8.5. A precipitate will form. This is filtered to prevent clogging the spray nozzles of either ground or air application equipment. The protein hydrolysate may be used full-strength or diluted to about 10% with water before the borate compound is added. The final proteinaceous bait spray may be used over wide inhabited areas, as the borates described above are exempt from tolerances for fire ant control (Fed. Reg. 58(124):34972 (Jun. 30, 1993)).

A second innovative method for use in accordance with this invention is to formulate the borax toxicant with an extender or gel, such as Min-U-Gel®, Thixcin E®, Myverol® and CAB-O-SIL®. These are commercially available. In this case, the precipitate is believed not to be important as gels are sprayed in a solid stream to adhere to tree trunks, telephones poles, buildings and so forth. The gels are formulated with synthetic bait and/or natural proteinaceous baits. This method of application reduces worker and public inconvenience of aerial spraying of large areas. For the homeowner, either the gel formulation or the liquid formulation may be applied to individual host trees for Tephritid fly control.

For lethal concentrations to reduce a Tephritidae fly population below economic threshold at a targeted area, a borax toxicant of the present invention should be applied once per week for at least six weeks (7 days per week). For lower concentrations which suppress egg production, a weekly application schedule for six weeks (7 days per week) is also believed to be necessary. These schedules are based on a life-span of about 40 days for Tephritidae fruit flies in the field and egg production suppression of at least 7 days. In a limited geographical area, these schedules are believed to be capable of suppressing fly populations below economic levels. With wide geographical use, it is also believed that Tephritidae fruit flies will be eradicated.

It, of course, should be understood by those versed in this art that the compositions of the present invention may be applied by any suitable means, such as by pressurized applications, hydraulic oil squirt cans and aerial sprays. Moreover, it should be appreciated by those skilled in this art that, whenever the compositions of the present invention are to be applied, weather conditions should be taken into account. For instance, treatment or retreatment should not be considered if weather reports indicate a 50% or greater chance of precipitation within 48 hours.

Overall, the more telling effects of use of the present invention are suppression of egg production which breaks the life cycle of the Tephritidae fruit flies, the lack of environmental effects of the treatment, and worker safety. Moreover, the present invention is adaptable to integrated pest management programs, and it is believed that the components and methods of the present invention do not attract honeybees.

The present invention will now be further illustrated, without limitation, with reference to the following examples.

EXAMPLE I

Agar is made as indicated below. Some difficulty, however, is encountered with about 0.25N and saturated agars. The agar makes a thick scum layer which rises to the top, but the agar is heated and stirred repeatedly until this layer seems to melt and be dispersed. Upon pouring these 2 agars, there appears to be some precipitation of either the agar or borax or both, but none can be seen upon gelling, unless the precipitate rises to the top with the foam. Each cage is set up with food and one cage is supplied with a "water only" agar patty and an agar patty with borax (control had 2 "water only" agar patties). Each cage contained 50 ♀ and 50 ♂.

The about 0.25N and saturated agars did not gel due to extreme pH. These two borax concentrations are not included and duplicate cages for control, about 0.01N and about 0.05N borax, are set up to run instead. Cages are set by about 4:45 pm on the first day, and the results are recorded in Table I below.

Borax* Toxicity Experiment with Borax Agar

| Molarity of Borax | Amount of Borax | Amount of Water | Amount of Agar |
|---|---|---|---|
| 0.005M | 0.572 gm | 300 ml | 3 gm |
| 0.025M | 2.861 gm | 300 ml | 3 gm |
| 0.12M | 14.303 gm | 300 ml | 3 gm |
| saturated | 115.0 gm | 500 ml | 3 gm |
| 0.0 | 0.0 | 300 ml | 3 gm |

*Borax (sodium tetraborate) $Na_2B_4O.10H_2O$ F.W. 381.37. About 1 g dissolves in about 16 ml water (0.164M_.

TABLE I

1. Results of three day experiment.*

| Day | Time | Cage # | Borax Concentration (N) | 72 Hr. Day 3 Dead ♀ | Dead ♂ | Age | No. of Eggs |
|---|---|---|---|---|---|---|---|
| Day 1 | 10:30 | A | 0.0-control | 0 | 0 | 9 days | 2553 |
| Day 1 | 10:30 | B | 0.02N | 0 | 0 | 9 days | 1072 |
| Day 1 | 10:39 | C | 0.10N | 2 | 13 | 9 days | 18 |
| Day 1 | 10:30 | D | 0.0-control | 0 | 0 | 9 days | 1064 |
| Day 1 | 10:40 | E | 0.02N | 1 | 3 | 9 days | 2165 |
| Day 1 | 10:45 | F | 0.10N | 5 | 21 | 9 days | 113 |

*Presumptive starting numbers, 50♂, 50♀ in each cage

EXAMPLE II

The agars, as prepared below, are used in the following five (5) Mortality and Egg Production Studies Measure about 30 ml of the agar described below into a graduated cylinder and pour into the bottom of a petri dish. This agar should be made daily. Weigh the agar patty on a sheet of glassine paper and leave this paper on the patty so it can be weighed later. Agar is placed on cages for about 24 hrs. then removed and weighed. Regular food is then placed on cages for the duration of the experiment.

| Borax (Sodium Tetraborate) Solutions for Toxicity Study $LC_{50}$ | | | | | |
|---|---|---|---|---|---|
| Normality (borax) | Weight | Volume | pH | % Wt/Vol | Molarity (borax) |
| 0.02N | 0.954 g | 500 ml | 9.19 | 0.1908% | 0.005 |
| 0.10N | 4.768 g | 500 ml | 9.26 | 0.9536% | 0.0250 |
| 0.20N | 9.535 g | 500 ml | 9.22 | 1.9% | 0.05 |
| 0.40N | 19.070 g | 500 ml | 9.32 | 3.8140% | 0.10 |
| 0.04N | 1.908 g | 500 ml | 9.04 | 0.3816% | 0.01 |
| 0.14N | 6.678 g | 500 ml | 9.17 | 1.3356% | 0.035 | about 0.05 g Agar  
about 2.0 g Yeast Hydrolysate  
about 55 ml distilled Water  
} combine ingredients and heat until the agar is melted (about 1 min.)

about 10.0 g Sugar  
} after the above is heated properly, add the sugar and stir until dissolved do not heat

1.a. Mortality and Egg Production Study #1

| Beginning Age | Cage # | Conc. of B(N) Borax(M) | Time Agar put on Cage | 24 hr | Dead ♂ | Dead ♀ |
|---|---|---|---|---|---|---|
| 10d | 1 | 0.0N-control | 3:50 pm | Day 1 | 0 | 1 |
| 10d | 2 | 0.02N (0.005M) | 3:55 pm | Day 1 | 1 | 1 |
| 10d | 3 | 0.02N (0.25M) | 4:00 pm | Day 1 | 1 | 0 |
| 10d | 4 | 0.20N (0.05M) | 4:05 pm | Day 1 | 21 | 5 |
| 10d | 5 | 0.40N (0.10M) | 4:10 pm | Day 1 | 24 | 10 |
| 11d | 6 | 0.0N-control | 11:11 am | Day 1 | 1 | 0 |
| 11d | 7 | 0.02N | 11:17 am | Day 1 | 0 | 0 |
| 11d | 8 | 0.10N | 11:25 am | Day 1 | 0 | 0 |
| 11d | 9 | 0.20N | 11:34 am | Day 1 | 8 | 1 |
| 11d | 10 | 0.40N | 11:38 am | Day 1 | 19 | 2 |
| 12d | 11 | 0.0N-control | 9:35 am | Day 1 | 0 | 0 |
| 12d | 12 | 0.02N | 9:38 am | Day 1 | 1 | 0 |
| 12d | 13 | 0.10N | 9:41 am | Day 1 | 0 | 0 |
| 12d | 14 | 0.20N | 9:45 am | Day 1 | 3 | 0 |
| 12d | 15 | 0.40N | 10:30 am | Day 1 | 12 | 4 |
| 2d | 1a | 0.0N-control | 8:30 am | Day 1 | 0 | 0 |
| 2d | 2a | 0.02N | 8:35 am | Day 1 | 0 | 0 |
| 2d | 3a | 0.10N | 8:40 am | Day 1 | 0 | 0 |
| 2d | 4a | 0.20N | 8:45 am | Day 1 | 0 | 1 |
| 2d | 5a | 0.40N | 8:50 am | Day 1 | 0 | 0 |
| 3d | 6a | 0.0N-control | 10:45 am | Day 1 | 0 | 0 |
| 3d | 7a | 0.02N | 10:47 am | Day 1 | 0 | 0 |
| 3d | 8a | 0.10N | 10:49 am | Day 1 | 0 | 0 |
| 3d | 9a | 0.02N | 10:51 am | Day 1 | 0 | 0 |
| 3d | 10a | 0.40N | 10:53 am | Day 1 | 4 | 1 |

1.b. Mortality and Egg Production Study #1

| Cage # | Total No. of Eggs | 48 hr | Dead ♂ | Dead ♀ | No. of Eggs | 72 hr | Dead ♂ | Dead ♀ | Total No. of Eggs |
|---|---|---|---|---|---|---|---|---|---|
| 1 | 844 | Day 2 | 0 | 0 | 615 | Day 3 | 0 | 0 | 541 |
| 2 | 787 | Day 2 | 0 | 0 | 472 | Day 3 | 0 | 2 | 98 |
| 3 | 0 | Day 2 | 13 | 0 | 1 | Day 3 | 6 | 0 | 13 |
| 4 | 3 | Day 2 | 4 | 17 | 2 | Day 3 | 0 | 2 | 0 |
| 5 | 1 | Day 2 | 1 | 15 | 4 | Day 3 | | | |
| 6 | 982 | Day 2 | 3 | 1 | 76 | Day 3 | 1 | 0 | 844 |
| 7 | 986 | Day 2 | 0 | 0 | 903 | Day 3 | 0 | 1 | 465 |
| 8 | 542 | Day 2 | 7 | 0 | 20 | Day 3 | 4 | 1 | 41 |
| 9 | 7 | Day 2 | 16 | 3 | 4 | Day 3 | 1 | 1 | 0 |
| 10 | 24 | Day 2 | 6 | 13 | 0 | Day 3 | 0 | 1 | 1 |
| 11 | 491 | Day 2 | 1 | 1 | 965 | Day 3 | 0 | 2 | 686 |
| 12 | 1330 | Day 2 | 0 | 0 | 902 | Day 3 | 0 | 0 | 668 |
| 13 | 287 | Day 2 | 9 | 0 | 41 | Day 3 | 5 | 2 | 95 |
| 14 | 121 | Day 2 | 12 | 6 | 0 | Day 3 | 10 | 8 | 20 |
| 15 | 1078 | Day 2* | 13 | 12 | 0 | Day 3 | 1 | 4 | 0 |

*9:45 am - only 6 total flies alive in cage 15 on Day 2

| 1a | 0 | Day 2 | 0 | 0 | 0 | Day 3 | 0 | 0 | 0 |
| 2a | 0 | Day 2 | 0 | 0 | 0 | Day 3 | 0 | 0 | 0 |
| 3a | 0 | Day 2 | 0 | 0 | 0 | Day 3 | 0 | 0 | 0 |
| 4a | 0 | Day 2 | 4 | 0 | 0 | Day 3 | 5 | 0 | 0 |
| 5a | 0 | Day 2 | 19 | 5 | 0 | Day 3 | 6 | 7 | 0 |
| 6a | 0 | Day 2 | 1 | 0 | 0 | Day 3 | 0 | 0 | 0 |
| 7a | 0 | Day 2 | 0 | 0 | 1 | Day 3 | 0 | 0 | 0 |
| 8a | 0 | Day 2 | 0 | 0 | 1 | Day 3 | 2 | 0* | 0 |
| 9a | 0 | Day 2 | 5 | 1 | 0 | Day 3 | 6 | 3 | 0 |
| 10a | 10 | Day 2 | 15 | 11 | 1 | Day 3 | 5 | 6 | 0 |

*one escape, sex not noted

1.c. Mortality and Egg Production Study #1

| Begn. Age | Cage # | Concentration of Borax | 96 hr | Dead ♂ | Dead ♀ | Total No. of Eggs | 120 hr | Dead ♂ | Dead ♀ | Total No. of Eggs |
|---|---|---|---|---|---|---|---|---|---|---|
| 10d | 1 | 0.0N-control | Day 4 | 0 | 0 | 632 | Day 5 | 0 | 0 | 882 |
| 10d | 2 | 0.02N | Day 4 | 1 | 1 | 206 | Day 5 | 0 | 1 | 512 |
| 10d | 3 | 0.10N | Day 4 | 1 | 3 | 32 | Day 5 | 0 | 9 | 31 |
| 10d | 4 | 0.20N | Day 4 | 0 | 1 | 0 | Day 5 | — | | — |
| 10d | 5 | 0.40N | Day 4 | — | | | Day 5 | — | | — |
| 11d | 6 | 0.0N-control | Day 4 | 0 | 0 | 754 | Day 5 | 0 | 1 | 1336 |
| 11d | 7 | 0.02N | Day 4 | 0 | 0 | 759 | Day 5 | 4 | 0 | 699 |
| 11d | 8 | 0.10N | Day 4 | 4 | 0 | 90 | Day 5 | 0 | 0 | 41 |
| 11d | 9 | 0.20N | Day 4 | 0 | 7 | 0 | Day 5 | 0 | 1 | 32 |
| 11d | 10 | 0.40N | Day 4 | 0 | 3 | 0 | Day 5 | 0 | 3 | 3 |
| 11d | 11 | 0.0N-control | Day 4 | 2 | 0 | 1126 | Day 5 | 1 | 1 | 436 |
| 12d | 12 | 0.02N | Day 4 | 1 | 1 | 1495 | Day 5 | 1 | 1 | 573 |
| 12d | 13 | 0.10N | Day 4 | 3 | 1 | 209 | Day 5 | 1 | 3 | 42 |
| 12d | 14** | 0.20N | Day 4 | 0 | 6 | 6 | Day 5 | 1 | 3 | 0 |
| 12d | 15** | 0.40N | Day 4 | 0 | 2 | 11 | Day 5 | 0 | 0 | 0 |

**Cage #14 destroyed on Day 5. Only 1 ♂ 2 ♀ was left alive.

| Begn. Age | Cage # | Concentration of Borax | 96 hr | Dead ♂ | Dead ♀ | Total No. of Eggs | 120 hr | Dead ♂ | Dead ♀ | Total No. of Eggs |
|---|---|---|---|---|---|---|---|---|---|---|
| 2d | 1a | control | Day 4 | 0 | 0 | 0 | Day 5 | 0 | 0 | 0 |
| 2d | 2a | 0.02N | Day 4 | 0 | 0 | 0 | Day 5 | 0 | 0 | 0 |
| 2d | 3a | 0.10N | Day 4 | 0 | 0 | 0 | Day 5 | 0 | 0 | 0 |
| 2d | 4a | 0.20N | Day 4 | 1 | 1 | 0 | Day 5 | 2 | 2 | 0 |
| 2d | 5a | 0.40N | Day 4 | 2 | 6 | 0 | Day 5 | 1 | 6 | 0 |
| 3d | 6a | control | Day 4 | 0 | 0 | 135 | Day 5 | 0 | 0 | 555 |
| 3d | 7a | 0.02N | Day 4 | 0 | 0 | 32 | Day 5 | 0 | 0 | 506 |
| 3d | 8a | 0.10N | Day 4 | 3 | 0 | 0 | Day 5 | 1 | 0 | 0 |
| 3d | 9a | 0.20N | Day 4 | 8 | 3 | 0 | Day 5 | 5 | 8 | 0 |
| 3d | 10a | 0.40N | Day 4 | 1 | 6 | 0 | Day 5 | — | 1 | 0 |

1.d. Mortality and Egg Production Study #1

| Begn. Age | Cage # | Boron (N) | 144 hr | Dead ♂ | Dead ♀ | Eggs | 168 hr | Dead ♂ | Dead ♀ | Total # of Eggs | Final Live Count |
|---|---|---|---|---|---|---|---|---|---|---|---|
| 10d | 1 | 0.0 control | Day 6 | 2 | 0 | 943 | Day 7 | 0 | 0 | 1283 | |
| 10d | 2 | 0.02 | Day 6 | 1 | 0 | 847 | Day 7 | 0 | 1 | 582 | |
| 10d | 3 | 0.10 | Day 6 | 0 | 3 | 22 | Day 7 | 0 | 1 | 0 | |
| 10d | 4 | terminated | Day 6 | — | — | — | — | — | — | — | |
| 10d | 5 | terminated | Day 6 | — | — | — | — | — | — | — | |
| 11d | 6 | 0.0 control | Day 6 | 0 | 1 | 956 | Day 7 | 0 | 0 | 988 | |
| 11d | 7 | 0.02 | Day 6 | 0 | 1 | 815 | Day 7 | 1 | 0 | 516 | |
| 11d | 8 | 0.10 | Day 6 | 0 | 0 | 81 | Day 7 | 1 | 0 | 201 | |
| 11d | 9 | 0.20 | Day 6 | 0 | 2 | 57 | Day 7 | 0 | 2 | 5 | |
| 11d | 10 | 0.40 | Day 6 | 0 | 0 | 0 | Day 7 | 0 | 3 | 0* | |
| 12d | 11 | 0.0 control | Day 6 | 0 | 0 | 1214 | Day 7 | 0 | 1 | 989* | ♂19/♀20 |
| 12d | 12 | 0.02 | Day 6 | 0 | 0 | 777 | Day 7 | 0 | 0 | 678* | ♂22/♀23 |
| 12d | 13 | 0.10 | Day 6 | 0 | 3 | 18 | Day 7 | 0 | 0 | —* | ♂12/♀16 |
| 12d | 14 | 0.20 | Day 6 | term'd Day 5 | | — | — | — | — | — | — |
| 12d | 15 | 0.40 | Day 6 | term'd Day 5 | | — | — | — | — | — | — |
| 2d | 1a | | Day 6 | 0 | 0 | 1505 | Day 7 | 0 | 0 | 955 | ♂25/♀25 |
| 2d | 2a | | Day 6 | 0 | 0 | 75 | Day 7 | 0 | 0 | 774 | ♂25/♀25 |
| 2d | 3a | | Day 6 | 1 | 0 | 16 | Day 7 | 0 | 0 | 119 | ♂24/♀25 |
| 2d | 4a | | Day 6 | 0 | 2 | 0 | Day 7 | 3 | 0 | 30 | ♂11/♀18 |
| 2d | 5a | | Day 6 | — | — | — | — | — | — | — | — |
| 3d | 6a | | Day 6 | 2 | 0 | 642 | Day 7 | 0 | 0 | 1001 | ♂22/♀25 |
| 3d | 7a | | Day 6 | 0 | 1 | 668 | Day 7 | 0 | 0 | — | ♂26/♀24 |
| 3d | 8a | | Day 6 | 1 | 2 | 20 | Day 7 | 0 | 0 | 202 | ♂18/♀24 |
| 3d | 9a | | Day 6 | 3 | 2 | 0 | Day 7 | — | 4 | 0 | ♂0/♀2 |
| 3d | 10a | | Day 6 | — | — | — | — | — | — | — | — |

*cages 10, 11, 12, 13 terminated as of the end of day 7

1.e. Mortality and Egg Production Study #1

| Cage # | Conc. Borax | | Dead ♂ | Dead ♀ | Live Final Total ♂ | Live Final Total ♀ | Total No. of Eggs |
|---|---|---|---|---|---|---|---|
| | | 216 hr | | | | | |
| 1 | control | Day 9 | 0 | 0 | 24 | 21 | 710* |
| 2 | 0.02N | Day 9 | 0 | 0 | 20 | 21 | 562* |
| 3 | 0.10N | Day 9 | — | 1 | | 1 | 0* |
| 4 | — | — | — | — | — | — | — |
| 5 | — | — | — | — | — | — | — |
| | | 192 hr | | | | | |
| 6 | control | Day 8 | 0 | 0 | 19 | 20 | 494** |
| 7 | 0.02N | Day 8 | 0 | 0 | 21 | 22 | —** |
| 8 | 0.10N | Day 8 | 2 | 0 | 7 | 22 | 279** |
| 9 | 0.20N | Day 8 | 0 | 0 | 0 | 7 | 0** |
| 10 | — | — | — | — | — | — | — |

*Terminated Day 9
**Terminated Day 8

2.a. Mortality and Egg Production Study #2

| Beginning Age | Cage # | Concen. Borax | Time Agar Put on Cage | 24 hr | ♂ | ♀ | 24 hr Total Wt. Paper Agar | Total No. of Eggs |
|---|---|---|---|---|---|---|---|---|
| 4d | 11 | control | 9:16 am | Day 1 | 0 | 0 | 16.5 g | 2 |
| 4d | 12 | 0.01N | 9:18 am | Day 1 | 0 | 1 | 17.7 g | 2 |
| 4d | 13 | 0.05N | 9:20 am | Day 1 | 0 | 0 | 19.8 g | 11 |
| 4d | 14 | 0.10N | 9:22 am | Day 1 | 1 | 0 | 21.7 g | 3 |
| 4d | 15 | 0.20N | 9:26 am | Day 1 | 7 | 3 | 21.0 g | 7 |
| 5d | 16 | control | 11:05 am | Day 1 | 0 | 0 | 21.9 g | 35 |
| 5d | 17 | 0.01N | 11:11 am | Day 1 | 0 | 0 | 21.7 g | 77 |
| 5d | 18 | 0.05N | 11:13 am | Day 1 | 0 | 0 | 22.7 g | 23 |
| 5d | 19 | 0.10N | 11:15 am | Day 1 | 0 | 0 | 22.1 g | 40 |
| 5d | 20 | 0.20N | 11:17 am | Day 1 | 3 | 0 | 21.5 g | 21 |
| 6d | 21 | control | 10:00 am | Day 1 | 0 | 0 | 15.6 g | 2008 |
| 6d | 22 | 0.01N | 10:02 am | Day 1 | 0 | 0 | 15.7 g | 770 |
| 6d | 23 | 0.05N | 10:04 am | Day 1 | 0 | 0 | 18.7 g | 630 |
| 6d | 24 | 0.10N | 10:10 am | Day 1 | 2 | 0 | 19.1 g | 263 |
| 6d | 25 | 0.20N | 10:45 am | Day 1 | 10 | 0 | 20.7 g | 150 |
| 7d | 26 | control | 10:24 am | Day 1 | 0 | 0 | 19.13 g | 697 |
| 7d | 27 | 0.02N | 10:26 am | Day 1 | 1 | 0 | 19.83 g | 820 |
| 7d | 28 | 0.10N | 10:28 am | Day 1 | 0 | 0 | 18.78 g | 433 |
| 7d | 29 | 0.20N | 10:30 am | Day 1 | 7 | 1 | 18.97 g | 477 |
| 7d | 30 | 0.20N | 10:32 am | Day 1 | 13 | 4 | 19.90 g | 0 |

2.b. Mortality and Egg Production Study #2

| Cage # | 48 hr | Dead ♂ | Dead ♀ | Total No. of Eggs | 72 hr | Dead ♂ | Dead ♀ | Total No. of Eggs |
|---|---|---|---|---|---|---|---|---|
| 11 | Day 2 | 0 | 0 | 0 | Day 3 | 1 | 0 | 29 |
| 12 | Day 2 | 0 | 0 | 0 | Day 3 | 0 | 0 | 13 |
| 13 | Day 2 | 0 | 0 | 0 | Day 3 | 2 | 0 | 0 |
| 14 | Day 2 | 10 | 4 | 0 | Day 3 | 8 | 3 | 0 |
| 15 | Day 2 | 14 | 12 | 0 | Day 3 | 2 | 9 | 0 |
| 16 | Day 2 | 0 | 0 | 813 | Day 3 | 0 | 0 | 719 |
| 17 | Day 2 | 0 | 0 | 1010 | Day 3 | 0 | 0 | 827 |
| 18 | Day 2 | 0 | 0 | 252 | Day 3 | 0 | 0 | 7 |
| 19 | Day 2 | 7 | 1 | 5 | Day 3 | 7 | 0 | 3 |
| 20 | Day 2 | 16 | 8 | 0 | Day 3 | 3 | 6 | 0 |
| 21 | Day 2 | 0 | 0 | 1099 | Day 3 | 0 | 0 | 1185 |
| 22 | Day 2 | 0 | 0 | 963 | Day 3 | 0 | 0 | 847 |
| 23 | Day 2 | 2 | 0 | 91 | Day 3 | 4 | 0 | 3 |

2.b. Mortality and Egg Production Study #2

| Cage # | 48 hr | Dead ♂ | Dead ♀ | Total No. of Eggs | 72 hr | Dead ♂ | Dead ♀ | Total No. of Eggs |
|---|---|---|---|---|---|---|---|---|
| 24 | Day 2 | 17 | 1 | 113 | Day 3 | 2 | 5 | 9 |
| 25 | Day 2 | 12 | 5 | 45 | Day 3 | 3 | 7 | 25 |
| 26 | Day 2 | 0 | 0 | 876 | Day 3 | 0 | 1 | 1528 |
| 27 | Day 2 | 0 | 0 | 702 | Day 3 | 1 | 1 | 1442 |
| 28 | Day 2 | 2 | 0 | 103 | Day 3 | 9 | 0 | 9 |
| 29 | Day 2 | 14 | 6 | 55 | Day 3 | 4 | 9 | 4 |
| 30 | Day 2 | 11 | 14 | 0 | Day 3 | — | 4 | 9 |

2.c. Mortality and Egg Production Study #2

| Beginning Age | Cage # | Concen. Borax | 96 hr | Dead ♂ | Dead ♀ | Total No. of Eggs | 120 hr | Dead ♂ | Dead ♀ | Total No. of Eggs |
|---|---|---|---|---|---|---|---|---|---|---|
| 4d | 11 | control | Day 4 | 0 | 0 | 606 | Day 5 | 0 | 0 | 1437 |
| 4d | 12 | 0.01N | Day 4 | 0 | 0 | 229 | Day 5 | 1 | 0 | 490 |
| 4d | 13 | 0.05N | Day 4 | 4 | 0 | 2 | Day 5 | 3 | 0 | 8 |
| 4d | 14 | 0.10N | Day 4 | 5 | 6 | 0 | Day 5 | 0 | 7 | 0 |
| 4d | 15 | 0.20N | Day 4 | 1 | 0 | 2 | Day 5 |  | 2 | 0 |
| 5d | 16 | control | Day 4 | 0 | 0 | 803 | Day 5 | 0 | 1 | 993 |
| 5d | 17 | 0.01N | Day 4 | 0 | 1 | 1143 | Day 5 | 1 | 0 | 1236 |
| 5d | 18 | 0.05N | Day 4 | 3 | 1 | 49 | Day 5 | 1 | 0 | 128 |
| 5d | 19 | 0.10N | Day 4 | 3 | 7 | 9 | Day 5 | 5 | 1 | 5 |
| 5d | 20 | 0.20N | Day 4 | 3 | 6 | 0 | Day 5 | — | 3 | 7 |
| 6d | 21 | control | Day 4 | 0 | 0 | 1289 | Day 5 | 0 | 0 | 2538 |
| 6d | 22 | 0.01N | Day 4 | 0 | 0 | 587 | Day 5 | 0 | 0 | 1587 |
| 6d | 23 | 0.5N | Day 4 | 6 | 0 | 6 | Day 5 | 1 | 0 | 10 |
| 6d | 24 | 0.10N | Day 4 | 2 | 4 | 10 | Day 5 | 1 | 2 | 4 |
| 6d | 25 | 0.20N | Day 4 | 0 | 4 | 32 | Day 5 | — | 4 | 3 |
| 7d | 26 | control | Day 4 | 0 | 0 | 1573 | Day 5 | 0 | 0 | 1054 |
| 7d | 27 | 0.01N | Day 4 | 0 | 1 | 1130 | Day 5 | 0 | 0 | 1103 |
| 7d | 28 | 0.05N | Day 4 | 3 | 1 | 0 | Day 5 | 4 | 6 | 4 |
| 7d | 29 | 0.10N | Day 4 | 0 | 4 | 1 | Day 5 | — | 2 | 6 |
| 7d | 30 | 0.40N | Day 4 | — | 3 | 5 | Day 5 | — | — | — |

2.d. Mortality and Egg Production Study #2

| Cage # | 144 hr | Dead ♂ | Dead ♀ | Total No. of Eggs | 168 hr | Dead ♂ | Dead ♀ | Total No. of Eggs | Final Live ♂ | Final Live ♀ |
|---|---|---|---|---|---|---|---|---|---|---|
| 11 | Day 6 | 0 | 0 | 1992 | Day 7 | 0 | 0 | 2044 | 24 | 25 |
| 12 | Day 6 | 0 | 0 | 998 | Day 7 | 0 | 1 | 1546 | 24 | 23 |
| 13 | Day 6 | 2 | 1 | 0 | Day 7 | 1 | 0 | 18 | 12 | 24 |
| 14 | Day 6 | 1 | 5 | 0 | Day 7 | — | — | — | — | — |
| 15 | Day 6 | — | — | — | — | — | — | — | — | — |
| 16 | Day 6 | 0 | 0 | 1556 | Day 7 | 0 | 0 | 735 | 25 | 24 |
| 17 | Day 6 | 0 | 1 | 1374 | Day 7 | 0 | 0 | 1007 | 24 | 23 |
| 18 | Day 6 | 1 | 2 | 310 | Day 7 | 0 | 0 | 376 | 21 | 22 |
| 19 | Day 6 | 1 | 7 | 1 | Day 7 | 1 | 5 | 2 | 0 | 4 |
| 20 | Day 6 | 0 | 1 | 0 | Day 7 | — | 1 | 0 | 0 | 0 |
| 21 | Day 6 | 0 | 0 | 2506 | Day 7 | 0 | 0 | 1964 | 25 | 25 |
| 22 | Day 6 | 0 | 0 | 2502 | Day 7 | 0 | 0 | 1610 | 25 | 24 |
| 23 | Day 6 | 0 | 0 | 34 | Day 7 | — | 0 | 99 | 7 | 23 |
| 24 | Day 6 | 0 | 2 | 13 | Day 7 | — | 1 | 7 | 0 | 11 |
| 25 | Day 6 | — | 4 | 0 | Day 7 | — | 2 | 0 | 0 | 0 |
| 26 | Day 6 | 0 | 0 |  | Day 7 | 0 | 0 | 956 | 25 | 24 |
| 27 | Day 6 | 0 | 0 |  | Day 7 | 0 | 0 | 912 | 23 | 23 |
| 28 | Day 6 | 0 | 0 |  | Day 7 | 1 | 2 | 0 | 6 | 16 |
| 29 | Day 6 | — | 3 |  | Day 7 | — | — | — | — | — |
| 30 | Day 6 | — | — | — | Day 7 | — | — | — | — | — |

3.a. Mortality and Egg Production Study #3

| Start Age in Days | Cage # | Concen. Borax | 24 hr | Dead ♂ | Dead ♀ | Total No. of Eggs | Eggs Per ♀ |
|---|---|---|---|---|---|---|---|
| 4d | 1 | control | Day 1 | 0 | 0 | 66 | 3 |
| 4d | 2 | 0.02N | Day 1 | 0 | 0 | 8 | 0 |
| 4d | 3 | 0.05N | Day 1 | 0 | 0 | 1 | 0 |
| 4d | 4 | 0.07N | Day 1 | 0 | 0 | 0 | 0 |
| 4d | 5 | 0.10N | Day 1 | 0 | 2 | 0 | 0 |
| 4d | 11 | control | Day 1 | 0 | 0 | 0 | 0 |
| 4d | 12 | 0.02N | Day 1 | 0 | 0 | 0 | 0 |
| 4d | 13 | 0.05N | Day 1 | 0 | 0 | 5 | 0 |
| 4d | 14 | 0.07N | Day 1 | 1 | 0 | 0 | 0 |
| 4d | 15 | 0.10N | Day 1 | 2 | 1 | 0 | 0 |
| 4d | 1a | control | Day 1 | 0 | 0 | 0 | 0 |
| 4d | 2a | 0.02N | Day 1 | 0 | 0 | 0 | 0 |
| 4d | 3a | 0.05N | Day 1 | 0 | 0 | 0 | 0 |
| 4d | 4a | 0.07N | Day 1 | 0 | 0 | 0 | 0 |
| 4d | 5a | 0.10N | Day 1 | 0 | 0 | D | 0 |
| 4d | 11a | control | Day 1 | 0 | 0 | 0 | 0 |
| 4d | 12a | 0.02N | Day 1 | 0 | 0 | 0 | 0 |
| 4d | 13a | 0.05N | Day 1 | 0 | 0 | 0 | 0 |
| 4d | 14a | 0.07N | Day 1 | 0 | 0 | 0 | 0 |
| 4d | 15a | 0.10N | Day 1 | 0 | 0 | 0 | 0 |

3.b. Mortality and Egg Production Study #3

| Cage # | 48 hr | Dead ♂ | Dead ♀ | Total No. of Eggs | Eggs Per ♀ | 72 hr | Dead ♂ | Dead ♀ | Total No. of Eggs | Eggs Per ♀ |
|---|---|---|---|---|---|---|---|---|---|---|
| 1 | Day 2 | 0 | 0 | 677 | 27 | Day 3 | 0 | 0 | 822 | 33 |
| 2 | Day 2 | 0 | 1 | 188 | 7 | Day 3 | 0* | 0 | 134 | 5 |
| 3 | Day 2 | 1 | 0 | 52 | 2 | Day 3 | 3 | 0 | 1 | 0 |
| 4 | Day 2 | 0 | 0 | 15 | 1 | Day 3 | 11 | 1 | 2 | 0 |
| 5 | Day 2 | 10 | 3 | 2 | 0 | Day 3 | 11 | 9 | 0 | 0 |
| 11 | Day 2 | 0 | 0 | 0 | 0 | Day 3 | 0 | 0 | 3 | 0 |
| 12 | Day 2 | 0 | 0 | 0 | 0 | Day 3 | 0 | 0 | 3 | 0 |
| 13 | Day 2 | 0 | 0 | 0 | 0 | Day 3 | 2 | 0 | 0 | 0 |
| 14 | Day 2 | 2 | 0* | 0 | 0 | Day 3 | 2 | 1 | 0 | 0 |
| 15 | Day 2 | 2 | 2 | 0 | 0 | Day 3 | 9 | 1 | 0 | 0 |
| 1a | Day 2 | 0 | 0 | 0 | 0 | Day 3 | 0 | 0 | 5 | 0 |
| 2a | Day 2 | 0 | 0 | 0 | 0 | Day 3 | 0 | 0 | 0 | 0 |
| 3a | Day 2 | 1 | 0 | 0 | 0 | Day 3 | 1 | 0 | 0 | 0 |
| 4a | Day 2 | 1 | 0 | 0 | 0 | Day 3 | 0 | 0 | 0 | 0 |
| 5a | Day 2 | 4 | 2 | 0 | 0 | Day 3 | 14 | 5 | 0 | 0 |
| 11a | Day 2 | 0 | 0 | 0 | 0 | Day 3 | 0 | 0 | 95 | 4 |
| 12a | Day 2 | 0 | 0 | 0 | 0 | Day 3 | 0 | 0 | 0 | 0 |
| 13a | Day 2 | 0 | 0 | 0 | 0 | Day 3 | 0 | 0 | 0 | 0 |
| 14a | Day 2 | 0 | 0 | 0 | 0 | Day 3 | 1 | 0 | 0 | 0 |
| 15a | Day 2 | 0 | 1 | 0 | 0 | Day 3 | 3 | 2 | 0 | 0 |

*1 escapee

3.c. Mortality and Egg Production Study #3

| Cage # | 96 hr | Dead ♂ | Dead ♀ | Total No. of Eggs | Eggs Per ♀ | 120 hr | Dead ♂ | Dead ♀ | Total No. of Eggs | Eggs Per ♀ |
|---|---|---|---|---|---|---|---|---|---|---|
| 1 | Day 4 | 1 | 0 | 669 | 27 | Day 5 | 0 | 0 | 827 | 33 |
| 2 | Day 4 | 1 | 1 | 235 | 9 | Day 5 | 1 | 0 | 522 | 22 |
| 3 | Day 4 | 3 | 1 | 0 | 0 | Day 5 | 4 | 0 | 0 | 0 |
| 4 | Day 4 | 5 | 3 | 0 | 0 | Day 5 | 8 | 5 | 0 | 0 |
| 5 | Day 4 | 3 | 9 | 0 | 0 | Day 5 | — | 2 | 0 | 0 |
| 11 | Day 4 | 0 | 0 | 511 | 20 | Day 5 | 1 | 0 | 1070 | 43 |
| 12 | Day 4 | 0 | 0 | 0 | 0 | Day 5 | 0 | 0 | 43 | 2 |
| 13 | Day 4 | 1 | 0 | 0 | 0 | Day 5 | 3 | 0 | 0 | 0 |
| 14 | Day 4 | 8 | 1 | 0 | 0 | Day 5 | 6 | 3 | 0 | 0 |
| 15 | Day 4 | 7 | 8 | 0 | 0 | Day 5 | 3 | 8 | 0 | 0 |
| 1a | Day 4 | 0 | 0 | 338 | 14 | Day 5 | 0 | 0 | 682 | 27 |

3.c. Mortality and Egg Production Study #3

| Cage # | 96 hr | Dead ♂ | Dead ♀ | Total No. of Eggs | Eggs Per ♀ | 120 hr | Dead ♂ | Dead ♀ | Total No. of Eggs | Eggs Per ♀ |
|---|---|---|---|---|---|---|---|---|---|---|
| 2a | Day 4 | 0 | 0 | 15 | 1 | Day 5 | 0 | 0 | 97 | 4 |
| 3a | Day 4 | 1 | 1 | 0 | 0 | Day 5 | 4 | 1 | 0 | 0 |
| 4a | Day 4 | 7 | 3 | 0 | 0 | Day 5 | 8 | 4 | 0 | 0 |
| 5a | Day 4 | 4 | 4 | 0 | 0 | Day 5 | 1 | 6 | 0 | 0 |
| 11a | Day 4 | 0 | 0 | 527 | 21 | Day 5 | 0 | 0 | 1082 | 43 |
| 12a | Day 4 | 0 | 0 | 0 | 0 | Day 5 | 0 | 0 | 0 | 0 |
| 13a | Day 4 | 1 | 1 | 0 | 0 | Day 5 | 1 | 0 | 0 | 0 |
| 14a | Day 4 | 7 | 0 | 0 | 0 | Day 5 | 11 | 3 | 0 | 0 |
| 15a | Day 4 | 7 | 3 | 0 | 0 | Day 5 | 6 | 10 | 0 | 0 |

3.d. Mortality and Egg Production Study #3

| Cage # | 144 hr | Dead ♂ | Dead ♀ | Total No. of Eggs | Eggs Per ♀ | 168 hr | Dead ♂ | Dead ♀ | Total No. of Eggs | Eggs Per ♀ | Live ♂ | Live ♀ | Begn. Total |
|---|---|---|---|---|---|---|---|---|---|---|---|---|---|
| 1 | Day 6 | 0 | 2 | 802 | 32 | Day 7 | 0 | 1 | 827 | 36 | 24 | 22 | 25♂/25♀ |
| 2 | Day 6 | 0 | 0 | 1092 | 46 | Day 7 | 0 | 0 | 940 | 39 | 21 | 24 | 24♂@/26♀ |
| 3 | Day 6 | 0 | 1 | 0 | 0 | Day 7 | 4 | 1 | 0 | 0 | 10 | 22 | 25♂/25♀ |
| 4 | Day 6 | 1 | 1 | 0 | 0 | Day 7 | — | 2 | 0 | 0 | — | 13 | 25♂/25♀ |
| 5 | Day 6 | — | 0 | 0 | 0 | Day 7 | — | 0 | 0 | 0 | — | 1 | 24♂/26♀ |
| 11 | Day 6 | 0 | 0 | 1990 | 80 | Day 7 | 0 | 0 | msg data | msg data | 25 | 25 | 26♂/25♀ |
| 12 | Day 6 | 0 | 1 | 214 | 9 | Day 7 | 0 | 1 | msg data | msg data | 25 | 23 | 25♂/25♀ |
| 13 | Day 6 | 0 | 1 | 0 | 0 | Day 7 | 0 | 0 | 0 | 0 | 19 | 25 | 25♂/26♀ |
| 14 | Day 6 | 1 | 4 | 0 | 0 | Day 7 | 2 | 7 | 0 | 0 | 3 | 7 | 25♂@/24♀ |
| 15 | Day 6 | 1 | 3 | 0 | 0 | Day 7 | — | 1 | 0 | 0 | — | 1 | 24♂/25♀ |
| 1a | Day 6 | 0 | 0 | 835 | 33 | Day 7 | 0 | 0 | 164 | 66 | 24 | 25 | 24♂/25♀ |
| 2a | Day 6 | 0 | 0 | 590 | 23 | Day 7 | 0 | 0 | 1373 | 53 | 29 | 26 | 29♂/26♀ |
| 3a | Day 6 | 2 | 1 | 0 | 0 | Day 7 | 0 | 1 | 0 | 0 | 16 | 21 | 25♂/25♀ |
| 4a | Day 6 | 4 | 6 | 0 | 0 | Day 7 | 1 | 1 | 0 | 0 | 4 | 11 | 25♂/25♀ |
| 5a | Day 6 | 1 | 8 | 0 | 0 | Day 7 | — | 1 | 0 | 0 | 0 | 0 | 24♂/26♀ |
| 11a | Day 6 | 0 | 0 | 1125 | 45 |  | 0 | 0 | 968 | 39 | 25 | 25 | 25♂/25♀ |
| 12a | Day 6 | 0 | 0 | 64 | 3 | Day 7 | 0 | 0 | 214 | 10 | 26 | 25 | 26♂/25♀ |
| 13a | Day 6 | 3 | 0 | 0 | 0 | Day 7 | 0 | 0 | 4 | 0 | 20 | 23 | 25♂/24♀ |
| 14a | Day 6 | 1 | 4 | 0 | 0 | Day 7 | 1 | 5 | 0 | 0 | 4 | 13 | 25♂/25♀ |
| 15a | Day 6 | 7 | 1 | 0 | 0 | Day 7 | —* | 1 | 0 | 0 | 0 | 7 | 23♂/25♀ |

*all males dead - Day 6
@1 escapee

4.a. Mortality and Egg Production Study #4

| Start Age in Days | Cage # | Concen. Borax | 24 hr | Dead ♂ | Dead ♀ | Total No. of Eggs | Eggs Per ♀ |
|---|---|---|---|---|---|---|---|
| 10d | 6 | control | Day 1 | 1 | 0 | 1002 | 40 |
| 10d | 7 | 0.02N | Day 1 | 0 | 0 | 590 | 24 |
| 10d | 8 | 0.05N | Day 1 | 1 | 0 | 549 | 22 |
| 10d | 9 | 0.07N | Day 1 | 3 | 0 | 555 | 23 |
| 10d | 10 | 0.10N | Day 1 | 4 | 1 | 345 | 14 |
| 10d | 16 | control | Day 1 | 0 | 0 | 1187 | 46 |
| 10d | 17 | 0.02N | Day 1 | 0 | 0 | 1139 | 48 |
| 10d | 18 | 0.05N | Day 1 | 3 | 0 | 538 | 22 |
| 10d | 19 | 0.07N | Day 1 | 7 | 0 | 597 | 24 |
| 10d | 20 | 0.10N | Day 1 | 13 | 1 | 542 | 23 |
| 10d | 6a | control | Day 1 | 0 | 1 | 1100 | 44 |
| 10d | 7a | 0.02N | Day 1 | 0 | 0 | 758 | 30 |
| 10d | 8a | 0.05N | Day 1 | 4 | 1 | 1412 | 54 |
| 10d | 9a | 0.07N | Day 1 | 2 | 2 | 901 | 38 |
| 10d | 10a | 0.10N | Day 1 | 7 | 0 | 756 | 30 |
| 10d | 16a | control | Day 1 | 0 | 0 | 1334 | 53 |
| 10d | 17a | 0.02N | Day 1 | 0 | 0 | 895 | 36 |
| 10d | 18a | 0.05N | Day 1 | 1 | 0 | 1169 | 47 |
| 10d | 19a | 0.07N | Day 1 | 5 | 0 | 618 | 25 |
| 10d | 20a | 0.10N | Day 1 | 8 | 1 | 1053 | 44 |

4.b. Mortality and Egg Production Study #4

| Cage # | 48 hr | Dead ♂ | Dead ♀ | Total No. of Eggs | Eggs Per ♀ | 72 hr | Dead ♂ | Dead ♀ | Total No. of Eggs | Eggs Per ♀ |
|---|---|---|---|---|---|---|---|---|---|---|
| 6 | Day 2 | 0 | 0 | 843 | 34 | Day 3 | 0 | 2 | 813 | 33 |
| 7 | Day 2 | 1 | 1 | 591 | 24 | Day 3 | 1 | 1 | 43 | 2 |
| 8 | Day 2 | 6 | 1 | 76 | 3 | Day 3 | 2 | 0 | 69 | 3 |
| 9 | Day 2 | 11 | 0 | 105 | 4 | Day 3 | 3 | 4 | 11 | 1 |
| 10 | Day 2 | 9 | 1 | 90 | 4 | Day 3 | 7 | 2 | 20 | 1 |
| 16 | Day 2 | 0 | 0 | 751 | 29 | Day 3 | 0 | 0 | 1253 | 48 |
| 17 | Day 2 | 0 | 0 | 111 | 5 | Day 3 | 0 | 0 | 10 | 0 |
| 18 | Day 2 | 5 | 0 | 122 | 5 | Day 3 | 0 | 1 | 18 | 1 |
| 19 | Day 2 | 9 | 0 | 92 | 4 | Day 3 | 6 | 3 | 23 | 1 |
| 20 | Day 2 | 11 | 4 | 24 | 1 | Day 3 | 1 | 1 | 2 | 0 |
| 6a | Day 2 | 0 | 0 | 492 | 21 | Day 3 | 0 | 0 | 959 | 40 |
| 7a | Day 2 | 0 | 0 | 66 | 3 | Day 3 | 1 | 0 | 60 | 2 |
| 8a | Day 2 | 8 | 0 | 96 | 4 | Day 3 | 3 | 0 | 63 | 3 |
| 9a | Day 2 | 11 | 0 | 44 | 2 | Day 3 | 3 | 0 | 68 | 3 |
| 10a | Day 2 | 15 | 6 | 50 | 2 | Day 3 | 3 | 1 | 20 | 1 |
| 16a | Day 2 | 0 | 0 | 850 | 34 | Day 3 | 0 | 0 | 838 | 34 |
| 17a | Day 2 | 0 | 0 | 175 | 7 | Day 3 | 0 | 0 | 69 | 3 |
| 18a | Day 2 | 6 | 0 | 61 | 2 | Day 3 | 1 | 0 | 15 | 1 |
| 19a | Day 2 | 16 | 0 | 53 | 2 | Day 3 | 3* | 0 | 39 | 2 |
| 20a | Day 2 | 17 | 7 | 52 | 2 | Day 3 | 0 | 6 | 41 | 3 |

*one escapee

4.c. Mortality and Egg Production Study #4

| Cage # | 96 hr | Dead ♂ | Dead ♀ | Total No. of Eggs | Eggs Per ♀ | 120 hr | Dead ♂ | Dead ♀ | Total No. of Eggs | Eggs Per ♀ |
|---|---|---|---|---|---|---|---|---|---|---|
| 6 | Day 4 | 1 | 0 | 840 | 37 | Day 5 | 1 | 0 | 863 | 38 |
| 7 | Day 4 | 0 | 0 | 12 | 1 | Day 5 | 1 | 0 | 52 | 3 |
| 8 | Day 4 | 5 | 2 | 12 | 1 | Day 5 | 2 | 4 | 7 | 0 |
| 9 | Day 4 | 4 | 2 | 4 | 0 | Day 5 | 1 | 0 | 0 | 0 |
| 10 | Day 4 | 2 | 0 | 28 | 1 | Day 5 | 2 | 6 | 6 | 0 |
| 16 | Day 4 | 0 | 0 | 1023 | 39 | Day 5 | 2 | 0 | 1349 | 52 |
| 17 | Day 4 | 2 | 2 | 12 | 1 | Day 5 | 1 | 0 | 0 | 0 |
| 18 | Day 4 | 8 | 0 | 2 | 0 | Day 5 | 4 | 0 | 0 | 0 |
| 19 | Day 4 | 3 | 2 | 5 | 0 | Day 5 | — | 5 | 0 | 0 |
| 20 | Day 4 | — | 6 | 7 | 0 | Day 5 | — | 4 | 0 | 0 |
| 6a | Day 4 | 1 | 0 | 860 | 36 | Day 5 | 0 | 1 | 685 | 29 |
| 7a | Day 4 | 1 | 0 | 8 | 0 | Day 5 | 1 | 0 | 50 | 2 |
| 8a | Day 4 | 3 | 0 | 9 | 0 | Day 5 | 4 | 0 | 0 | 0 |
| 9a | Day 4 | 2 | 0 | 0 | 0 | Day 5 | 3 | 1 | 0 | 0 |
| 10a | Day 4 | — | 4 | 0 | 0 | Day 5 | — | 3 | 0 | 0 |
| 16a | Day 4 | 0 | 0 | 676 | 27 | Day 5 | 0 | 0 | 613 | 25 |
| 17a | Day 4 | 2 | 0 | 17 | 1 | Day 5 | 2 | 1 | 36 | 1 |
| 18a | Day 4 | 2 | 1 | 0 | 0 | Day 5 | 1 | 0 | 5 | 0 |
| 19a | Day 4 | 0 | 3 | 0 | 0 | Day 5 | 0 | 1 | 3 | 0 |
| 20a | Day 4 | 1 | 0 | 0 | 0 | Day 5 | — | 4 | 0 | 0 |

4.d. Mortality and Egg Production Study #4

| Cage # | 144 hr | Dead ♂ | Dead ♀ | Total # of Eggs | Eggs Per ♀ | 168 hr | Dead ♂ | Dead ♀ | Total No. of Eggs | Eggs Per ♀ | Live ♂ | Live ♀ | |
|---|---|---|---|---|---|---|---|---|---|---|---|---|---|
| 6 | Day 6 | 0 | 0 | 564 | 25 | Day 7 | 1 | 0 | 1057 | 46 | 21 | 23 | 25♂/25♀ |
| 7 | Day 6 | 0 | 0 | 141 | 6 | Day 7 | 0 | 0 | 368 | 16 | 22 | 23 | 25♂/25♀ |
| 8 | Day 6 | 5 | 0 | 8 | 0 | Day 7 | 0 | 1 | 7 | 0 | 4 | 17 | 25♂/25♀ |
| 9 | Day 6 | 1 | 2 | 0 | 0 | Day 7 | 1 | 6 | 0 | 0 | 1 | 10 | 25♂/24♀ |
| 10 | Day 6 | — | 3 | 0 | 0 | Day 7 | — | 4 | 1 | 0 | — | 7 | 24♂/24♀ |
| 16 | Day 6 | 0 | 0 | 1125 | 43 | Day 7 | 0 | 0 | 771 | 30 | 22 | 26 | 24♂/26♀ |
| 17 | Day 6 | 1 | 1 | 0 | 0 | Day 7 | 2 | 0 | 0 | 0 | 18 | 21 | 24♂/24♀ |
| 18 | Day 6 | 0 | 2 | 0 | 0 | Day 7 | 0 | 0 | 0 | 0 | 5 | 21 | 25♂/24♀ |

4.d. Mortality and Egg Production Study #4 -continued

| Cage # | 144 hr | Dead ♂ | Dead ♀ | Total # of Eggs | Eggs Per ♀ | 168 hr | Dead ♂ | Dead ♀ | Total No. of Eggs | Eggs Per ♀ | Live ♂ | Live ♀ | |
|---|---|---|---|---|---|---|---|---|---|---|---|---|---|
| 19 | Day 6 | — | 6 | 6 | 0 | Day 7 | all ♂ dead | 2 | 0 | 0 | 0 | 7 | 25♂/25♀ |
| 20 | Day 6 | — | 2 | 0 | 0 | Day 7 | all ♂ dead | 3 | 0 | 0 | 0 | 3 | 25♂/24♀ |
| 6a | Day 6 | 0 | 0 | 327 | 14 | Day 7 | 1 | 1 | 219 | 10 | 23 | 22 | 25♂/25♀ |
| 7a | Day 6 | 4 | 0 | 55 | 2 | Day 7 | 0 | 0 | 141 | 6 | 18 | 25 | 25♂/25♀ |
| 8a | Day 6 | 3 | 1 | 0 | 0 | Day 7 | 3 | 1 | 0 | 0 | 5 | 23 | 33♂/26♀ |
| 9a | Day 6 | 3 | 1 | 0 | 0 | Day 7 | 1 | 0 | 0 | 0 | 0 | 20 | 25♂/24♀ |
| 10a | Day 6 | — | 8 | 0 | 0 | Day 7 | all ♂ dead | 3 | 0 | 0 | 0 | 0 | 25♂/25♀ |
| 16a | Day 6 | 0 | 1 | missing data | — | Day 7 | 0 | 1 | 450 | 19 | 25 | 23 | 25♂/25♀ |
| 17a | Day 6 | 1 | 1 | missing data | — | Day 7 | 0 | 0 | 155 | 7 | 20 | 23 | 25♂/25♀ |
| 18a | Day 6 | 0 | 0 | missing data | — | Day 7 | 0 | 2 | 49 | 2 | 14 | 22 | 25♂/25♀ |
| 19a | Day 6 | 1 | 3 | 0 | 0 | Day 7 | — | 3 | 0 | 0 | 0 | 15 | 26♂*/25♀ |
| 20a | Day 6 | all ♂ dead | 3 | 0 | 0 | Day 7 | — | 1 | 0 | 0 | 0 | 2 | 26♂/24♀ |

*1 escapee

5.a. Mortality and Egg Production Study #5

| Start Age in Days | Cage # | Concen. Borax | 24 hr | Dead ♂ | Dead ♀ | Total No. of Eggs | Eggs Per ♀ |
|---|---|---|---|---|---|---|---|
| 4d | 21 | control | Day 1 | 0 | 0 | 0 | 0 |
| 4d | 22 | 0.02N | Day 1 | 0 | 0 | 0 | 0 |
| 4d | 23 | 0.05N | Day 1 | 0 | 1 | 0 | 0 |
| 4d | 24 | 0.07N | Day 1 | 0 | 0 | 0 | 0 |
| 4d | 25 | 0.10N | Day 1 | 1 | 0 | 0 | 0 |
| 10d | 26 | control | Day 1 | 0 | 0 | 380 | 16 |
| 10d | 27 | 0.02N | Day 1 | 1 | 0 | 162 | 7 |
| 10d | 28 | 0.05N | Day 1 | 1 | 0 | 231 | 9 |
| 10d | 29 | 0.07N | Day 1 | 3 | 0 | 164 | 7 |
| 10d | 30 | 0.10N | Day 1 | 9 | 0 | 211 | 9 |
| 4d | 1 | control | Day 1 | 1 | 0 | 0 | 0 |
| 4d | 2 | 0.02N | Day 1 | 0 | 0 | 0 | 0 |
| 4d | 3 | 0.05N | Day 1 | 0 | 0 | 0 | 0 |
| 4d | 4 | 0.07N | Day 1 | 1 | 0 | 0 | 0 |
| 4d | 5 | 0.10N | Day 1 | 2 | 0 | 0 | 0 |
| 10d | 6 | control | Day 1 | 0 | 0 | 1769 | 74 |
| 10d | 7 | 0.02N | Day 1 | 0 | 0 | 0 | 0 |
| 10d | 8 | 0.05N | Day 1 | 4 | 0 | 8 | 0 |
| 10d | 9 | 0.07N | Day 1 | 5 | 0 | 341 | 14 |
| 10d | 10 | 0.20N | Day 1 | 16 | 1 | 0 | 0 |

5.b. Mortality and Egg Production Study #5

| Cage # | 48 hr | Dead ♂ | Dead ♀ | Total No. of Eggs | Eggs Per ♀ | 72 hr | Dead ♂ | Dead ♀ | Total No. of Eggs | Eggs Per ♀ |
|---|---|---|---|---|---|---|---|---|---|---|
| 21 | Day 2 | 0 | 0 | 0 | 0 | Day 3 | 0 | 1 | 64 | 3 |
| 22 | Day 2 | 0 | 0 | 0 | 0 | Day 3 | 0 | 1 | 0 | 0 |
| 23 | Day 2 | 0 | 0 | 0 | 0 | Day 3 | 3 | 0 | 0 | 0 |
| 24 | Day 2 | 3 | 0 | 0 | 0 | Day 3 | 7 | 1 | 0 | 0 |
| 25 | Day 2 | 12 | 2 | 0 | 0 | Day 3 | 10 | 5 | 0 | 0 |
| 26 | Day 2 | 0 | 0 | 691 | 29 | Day 3 | 1 | 1 | 460 | 19 |
| 27 | Day 2 | 0 | 0 | 450 | 18 | Day 3 | 1 | 0 | 127 | 5 |
| 28 | Day 2 | 6 | 0 | 169 | 7 | Day 3 | 5 | 1 | 9 | 0 |
| 29 | Day 2 | 8 | 0 | 93 | 4 | Day 3 | 8 | 2 | 36 | 2 |
| 30 | Day 2 | 9 | 4 | 91 | 4 | Day 3 | 3 | 2 | 39 | 2 |
| 1 | Day 2 | 1 | 1 | 0 | 0 | Day 3 | 1 | 0 | 236 | 10 |
| 2 | Day 2 | 0 | 0 | 0 | 0 | Day 3 | 2 | 0 | 0 | 0 |
| 3 | Day 2 | 2 | 0 | 0 | 0 | Day 3 | 8 | 0 | 0 | 0 |
| 4 | Day 2 | 2 | 0 | 0 | 0 | Day 3 | 5 | 2 | 0 | 0 |
| 5 | Day 2 | 11 | 3 | 0 | 0 | Day 3 | 11 | 5 | 0 | 0 |
| 6 | Day 2 | 0 | 0 | 371 | 16 | Day 3 | 0 | 0 | 563 | 24 |
| 7 | Day 2 | 8 | 0 | 42 | 2 | Day 3 | 5 | 0 | 120 | 5 |
| 8 | Day 2 | 16 | 2 | 21 | 1 | Day 3 | 3 | 1 | 12 | 1 |
| 9 | Day 2 | 13 | 2 | 101 | 4 | Day 3 | 2 | 1 | 46 | 2 |
| 10 | Day 2 | 9 | 15 | 12 | 1 | Day 3 | all ♂ dead Day 2 | 4 | 0 | 0 |

5.c. Mortality and Egg Production Study #5

| Cage # | 96 hr | Dead ♂ | Dead ♀ | Total No. of Eggs | Eggs Per ♀ | 120 hr | Dead ♂ | Dead ♀ | Total No. of Eggs | Eggs Per ♀ |
|---|---|---|---|---|---|---|---|---|---|---|
| 21 | Day 4 | 0 | 0 | 270 | 11 | Day 5 | 0 | 0 | 420 | 18 |
| 22 | Day 4 | 0 | 0 | 0 | 0 | Day 5 | 0 | 0 | 0 | 0 |
| 23 | Day 4 | 6 | 2 | 0 | 0 | Day 5 | 6 | 1 | 0 | 0 |
| 24 | Day 4 | 6 | 4 | 0 | 0 | Day 5 | 5 | 6 | 0 | 0 |
| 25 | Day 4 | 2 | 8 | 0 | 0 | Day 5 | — | 5 | 0 | 0 |
| 26 | Day 4 | 0 | 0 | 698 | 30 | Day 5 | 1 | 0 | 1158 | 50 |
| 27 | Day 4 | 0 | 0 | 107 | 4 | Day 5 | 0 | 0 | 252 | 10 |
| 28 | Day 4 | 5 | 0 | 0 | 0 | Day 5 | 3 | 0 | 0 | 0 |
| 29 | Day 4 | 5 | 0 | 9 | 0 | Day 5 | 0 | 4 | 0 | 0 |
| 30 | Day 4 | 2 | 1 | 10 | 1 | Day 5 | 2 | 4 | 0 | 0 |
| 1 | Day 4 | 0 | 0 | 394 | 16 | Day 5 | 0 | 0 | missing data | missing data |
| 2 | Day 4 | 2 | 0 | 0 | 0 | Day 5 | 0 | 0 | 8 | 0 |
| 3 | Day 4 | 8 | 7 | 0 | 0 | Day 5 | 7 | 10 | 12 | 1 |
| 4 | Day 4 | 13 | 7 | 0 | 0 | Day 5 | 3 | 6 | 2 | 0 |
| 5 | Day 4 | 2 | 9 | 0 | 0 | Day 5 | all ♂ dead Day 4 | 1 | 0 | 0 |
| 6 | Day 4 | 1 | 1 | 442 | 18 | Day 5 | 0 | 0 | 617 | 27 |
| 7 | Day 4 | 6 | 0 | 43 | 2 | Day 5 | 4 | 1 | 8 | 0 |
| 8 | Day 4 | 2 | 10 | 35 | 2 | Day 5 | — | 3 | 19 | 2 |
| 9 | Day 4 | 4 | 5 | 23 | 1 | Day 5 | 1 | 6 | 0 | 0 |
| 10 | Day 4 | — | 3 | 0 | 0 | Day 5 | — | 2 | 0 | 0 |

5.d. Mortality and Egg Production Study #5

| Cage # | 144 hr | Dead ♂ | Dead ♀ | Total # of Eggs | Eggs/ ♀ | 168 hr | Dead ♂ | Dead ♀ | Total # of Eggs | Eggs Per ♀ | Live ♂ | Live ♀ | Total ♂ | Total ♀ |
|---|---|---|---|---|---|---|---|---|---|---|---|---|---|---|
| 21 | Day 6 | 0 | 0 | 1017 | 42 | Day 7 | 0 | 0 | 601 | 25 | 25 | 24 | 25 | 25 |
| 22 | Day 6 | 1 | 0 | 4 | 0 | Day 7 | 0 | 0 | 30 | 1 | 24 | 24 | 25 | 25 |
| 23 | Day 6 | 7 | 3 | 0 | 0 | Day 7 | 0 | 4 | 0 | 0 | 2 | 14 | 24 | 25 |
| 24 | Day 6 | 4 | 7 | 0 | 0 | Day 7 | — | 3 | 0 | 0 | 0 | 4 | 25 | 25 |
| 25 | Day 6 | — | 4 | 0 | 0 | Day 7 | — | —* | — | — | 0 | 0 | 25 | 24 |
| 26 | Day 6 | 0 | 0 | 780 | 34 | Day 7 | 0 | 2 | 1427 | 62 | 23 | 21 | 25 | 24 |
| 27 | Day 6 | 0 | 0 | 318 | 13 | Day 7 | 0 | 0 | 1069 | 43 | 23 | 25 | 25 | 25 |
| 28 | Day 6 | 0 | 0 | 0 | 0 | Day 7 | 2 | 1 | 0 | 0 | 2 | 23 | 24 | 25 |
| 29 | Day 6 | 1 | 4 | 0 | 0 | Day 7 | 0 | 1 | 0 | 0 | 0 | 13 | 25 | 24 |
| 30 | Day 6 | —@ | 0 | 0 | 0 | Day 7 | — | 3 | 0 | 0 | 0 | 10 | 25 | 24 |
| 1 | Day 6 | 0 | 0 | 702 | 29 | Day 7 | 1 | 0 | 651 | 27 | 21 | 24 | 25 | 25 |
| 2 | Day 6 | 2 | 0 | 31 | 1 | Day 7 | 0 | 0 | 115 | 5 | 18 | 24 | 24 | 24 |
| 3 | Day 6 | — | 3 | 0 | 0 | Day 7 | — | 2 | 0 | 0 | 0 | 3 | 25 | 25 |
| 4 | Day 6 | 0 | 2 | 0 | 0 | Day 7 | 1 | 2 | 0 | 0 | 0 | 8 | 25 | 27 |
| 5 | Day 6 | — | 2 | 0 | 0 | Day 7 | — | 3 | 0 | 0 | 0 | 1 | 26 | 24 |
| 6 | Day 6 | 1 | 0 | 576 | 25 | Day 7 | 1 | 0 | 1097 | 48 | 23 | 23 | 26 | 24 |
| 7 | Day 6 | 0 | 2 | 0 | 0 | Day 7 | 1 | 3 | 0 | 0 | 1 | 20 | 25 | 26 |
| 8 | Day 6 | — | 7 | 0 | 0 | Day 7 | — | 3 | 0 | 0 | 0 | 1 | 25 | 25 |
| 9 | Day 6 | — | 6 | 0 | 0 | Day 7 | — | 4 | 0 | 0 | 0 | 0 | 25 | 24 |
| 10 | Day 6 | — | — | — | — | Day 7 | — | — | 0 | — | 0 | 0 | 25 | 25 |

*5 female left alive (1)
@all ♂ dead — Day 6

EXAMPLE III

Examples of various formulations that may be utilized in accordance with the present invention include:

1.) 6% borax, 1% agar and 94% water, wherein the agar and water are combined, i.e., the 94% water and 1% agar, and brought to a boil. The mixture is removed from the heat and the borax is added. This results in a gelatinous mixture which will not dry completely and which is believed will adhere to trees, buildings, etc. to which it is applied. It may be applied by spraying via a pressurized application or an hydraulic oil squirt can to utility poles, trees, fences, etc.

2.) 6% borax, 1% agar and 93% proteinaceous bait (10% (Miller's Nu-Lure®), wherein the proteinaceous bait is formulated with 90 parts water and 10 parts proteinaceous concentrated bait. This formulation 2 is made as formulation 1 above and may be applied similarly; however, this formulation 2 is believed to be a better attractant than formulation 1;

3.) 1% borax, 76% proteinaceous bait (Miller's Nu-Lure®) and 23% Min-U-Gel® (Floridin Co.), wherein this formulation 3 is made following the steps to make formulation 1, except without heating. This formulation 3 may be applied like formulations 1 and 2, i.e., simply mix and spray.

4.) 6% borax, 70% proteinaceous bait (Miller's Nu-Lure®) and 23% Min-U-Gel® (Floridin Co.), wherein this formulation 4 is made following the steps to make formulation 1, except without heating. This formulation 4 may be applied like formulations 1 and 2, i.e., simply mix and spray.

5.) 1% borax and 99% Min-U-Gel®(Floridin Co.) or 6% borax and 94% Min-U-Gel® (Floridin Co.), wherein these formulations are made following the steps to make formulation 1, except without heating. These two formulations may be applied like formulations 1 and 2, i.e., simply mix and spray.

The proper viscosity of each formulation should be maintained, i.e., the surface of a spot application is thick enough to hold indentations, to avoid splashback, runoff and possible ineffective treatments on new porous surfaces. Generally, 23% of Min-U-Gel® (Floridin Co.) is believed to be sufficient to maintain appropriate viscosity, however, additional or lesser amounts may be necessary to achieve desired results.

To treat infested area via spot treatment: apply one or more of the above formulations, e.g., formulations 3–5, with a pressurized application or a hydraulic oil squirt can to, e.g., utility poles, trees, fences, signs, etc. At least about 600 evenly distributed bait spots per squire mile, or approximately 60 to 80 bait spots per city block. Apply treatment once per week for at least about six weeks. The area of coverage will extend about nine square miles around each fly find.

As opposed to spot treatment, the above formulations, e.g., formulations 3–5, may be squirted on tree trunks, fences, utility poles, signs, etc. in areas thereon which are out of reach of children at a rate of about 0.1 oz to about 0.2 oz (about 3 to about 5 ml) per station.

With respect to aerial treatment or retreatment of the above formulations, such as formulations 1 and 2 above, it should not be considered if weather reports indicate a 50% or greater chance of precipitation within 48 hours. Applications of full coverage of the bait sprays, such as formulations 1 and 2 above, should be scheduled approximately once per week for at least six weeks. It is believed that the bait formulations of the present invention, such as bait formulations 1 and 2 identified above in this Example, are effective as full coverage aerial bait sprays when applied in amounts on the order of between about 5 oz and about 128 oz or more per acre per full coverage application. It should, of course, be understood that the amount of bait formulation actually applied will depend upon the objectives to be accomplished and the size of the area to be covered, Moreover, the area of full coverage spray should extend a minimum of about 1.5 miles beyond known fruit fly infestation. It, of course, may be expanded to about 2.5 miles from any kind if the infestation is heavy. Weather conditions may also dictate change in spray schedules. After an estimated two off generations of negative trapping, spray operations may be discontinued.

The present invention may, of course, be carried out in other specific ways than those herein set forth without departing from the spirit and essential characteristics of the invention. The present embodiments are, therefore, to be considered in all respects as illustrative and not restrictive and all changes coming within the spirit and scope of the appended claims are intended to be embraced herein.

Having described our invention, we claim:

1. A method of treating fruit flies of the Tephritidae family so that the fruit flies die prematurely, said method comprising:
feeding to the fruit flies an effective fruit fly controlling amount of a borax toxicant to cause the fruit flies to die prematurely, so that following ingestion of the borax toxicant by the fruit flies, the fruit flies will die prematurely due to the ingestion of the borax toxicant.

2. A method of claim 1, the borax toxicant being borax.

3. A method of claim 2, said feeding comprises feeding the fruit flies between about 5 mM and about 10 mM of borax within about a 24 hour period.

4. A method of claim 2 wherein the effective amount is in the range of between about 0.01M and about 0.12M.

5. A method of claim 1, the borax toxicant being selected from the group consisting of borax, anhydrous borax, ammonium tetraborate, ammonium pentaborate, potassium pentaborate, potassium tetraborate, sodium metaborate, disodium tetraborate decahydrate, disodium tetraborate pentahydrate and disodium octaborate tetrahydrate.

6. A method of claim 1 wherein the borax toxicant is included in a bait.

7. A method of interfering with reproduction by female fruit flies of the Tephriditae family so that the female fruit flies will stop producing eggs for about 7 days or longer, said method comprising:
feeding to the female fruit flies an effective fruit fly controlling amount of a borax toxicant to interfere with the reproduction by the female fruit flies, so that following ingestion of the borax toxicant by the female fruit flies, the female fruit flies will stop producing eggs for a period of about 7 days or more due to the ingestion of the borax toxicant.

8. A method of claim 7, the borax toxicant being borax.

9. A method of claim 8, said feeding comprises feeding the fruit flies between about 2.5 mM and about 5 mM of borax within about a 24 hour period.

10. A method of claim 8 wherein the effective amount is in the range of between about 0.01M and about 0.12M.

11. A method of claim 7, the borax toxicant being selected from the group consisting of borax, anhydrous borax, ammonium tetraborate, ammonium pentaborate, potassium pentaborate, potassium tetraborate, sodium metaborate, disodium tetraborate decahydrate, disodium tetraborate pentahydrate and disodium octaborate tetrahydrate.

12. A method of claim 7, wherein the borax toxicant is included in a bait.

13. A method of reducing the population of fruit flies of the Tephritidae family at a targeted area, said method comprising:
applying to the targeted area an effective fruit fly controlling amount of a borax toxicant for ingestion by the fruit flies at the targeted area, so that following ingestion of the borax toxicant by the fruit flies, the population is reduced at the targeted area due to of the ingestion of the borax toxicant.

14. A method of claim 13, the borax toxicant being borax.

15. A method of claim 14 wherein the ingestion by the fruit flies is between about 2.5 mM and about 10 mM of borax within about a 24 hour period.

16. A method of claim 15, said application of the borax toxicant at the targeted area being done at least about once per week for at least about six weeks.

17. A method of claim 14 wherein the ingestion by the fruit flies is between about 5 mM and about 10 mM of borax within about a 24 hour period.

18. A method of claim 17, said application of the borax toxicant at the targeted area being done at least about once per week for at least about six weeks.

19. A method of claim 14 wherein the effective amount is in the range of between about 0.01M and about 0.12M.

20. A method of claim 13, the borax toxicant being selected from the group consisting of borax, anhydrous borax, ammonium tetraborate, ammonium pentaborate, potassium pentaborate, potassium tetraborate, sodium metaborate, disodium tetraborate decahydrate, disodium tetraborate pentahydrate and disodium octaborate tetrahydrate.

21. A method of claim 13, wherein the borax toxicant is included in a bait.

22. A bait or lure for reducing the number of fruit flies of the Tephritidae family, said bait or lure consisting essentially of a borax toxicant, said borax toxicant being present in said bait or lure in an effective fruit fly controlling amount so that following ingestion of said borax toxicant in said bait or lure by the fruit flies, the number of fruit flies is reduced due to the consumption of said borax toxicant by the fruit flies.

23. A bait or lure of claim 22, said bait or lure being in a form selected from the group consisting of a patty, cream, pellet, gel, foam, paste, liquid and spray.

24. A bait or lure of claim 22, said bait or lure further including a bait selected from the group consisting of a protein hydrolysate bait and a synthetic.

25. A bait or lure of claim 22, said bait or lure further including other ingredients selected from the group consisting of agar, insecticide, liquefier, sweetener and carrier.

26. A bait or lure of claim 22, said borax toxicant being borax.

27. A bait or lure of claim 26 wherein the consumption by the fruit flies is between about 2.5 mM and about 10 mM of borax within about a 24 hour period.

28. A bait or lure of claim 26 wherein the effective amount is in the range of between about 0.01M and about 0.12M.

29. A bait or lure of claim 26, said bait or lure further including agar, yeast hydrolysate, sugar and water.

30. A bait or lure of claim 22, the borax toxicant being selected from the group consisting of borax, anhydrous borax, ammonium tetraborate, ammonium pentaborate, potassium pentaborate, potassium tetraborate, sodium metaborate, disodium tetraborate decahydrate, disodium tetraborate pentahydrate and disodium octaborate tetrahydrate.

* * * * *

UNITED STATES PATENT AND TRADEMARK OFFICE
CERTIFICATE OF CORRECTION

PATENT NO. : 5,698,208
DATED : December 16, 1997
INVENTOR(S) : Herbert N. Nigg and Samuel E. Simpson It is certified that error appears in the above-identified patent and that said Letters Patent is hereby corrected as shown below:

Column 1, line 45: "mixed With more" should read --mixed with more--; and line 47: "realrose" should read --maltose--.

Column 6, line 40: "(0.164M_." should read --(0.164M)..

Col. 8, Chart 1.b, 6th Col., line 6: "76" should read --764--;

Chart 1.b, bottom line: "*one escape, sex" should read --*one escapee, sex--.

Col. 9, Chart 1.c, 1st Col, line 11: "11d" should read --12d--; and

Chart 1.c, line 16: "Cage #14 destroyed on Day 5. Only 1 2 was left alive." should read --Cage #14 destroyed on Day 5. Only 1 ♂ 2♀ was left alive *Cage #15 destroyed on Day 5. Only 1♀ left alive--.

Column 16, Chart 3a, 7th Col., line 5: "D"should read --0--.

Signed and Sealed this

Fifth Day of May, 1998

BRUCE LEHMAN

*Attest:*

*Attesting Officer*      Commissioner of Patents and Trademarks

UNITED STATES PATENT AND TRADEMARK OFFICE
CERTIFICATE OF CORRECTION

PATENT NO.    : 5,698,208
DATED         : December 16, 1997
INVENTOR(S)   : Herbert N. Nigg and Samuel E. Simpson It is certified that error appears in the above-identified patent and that said Letters Patent is hereby corrected as shown below:

<u>Column 27,</u>
Line 19, "a synthetic." should be -- a synthetic bait. --

Signed and Sealed this

Twenty-first Day of May, 2002

Attest:

JAMES E. ROGAN
*Attesting Officer*     *Director of the United States Patent and Trademark Office*